United States Patent [19]

Matsuo et al.

[11] Patent Number: 4,885,297
[45] Date of Patent: Dec. 5, 1989

[54] THIAZOLOPYRIDINE COMPOUNDS, PROCESSES FOR THE PREPARATION THEREOF AND PHARMACEUTICAL COMPOSITION COMPRISING THE SAME

[75] Inventors: Masaaki Matsuo, Toyonaka; Daizo Morino, Matsubara; Kiyoshi Tsuji, Kishiwada; Hiroyuki Okumura, Ibaraki, all of Japan

[73] Assignee: Fujisawa Pharmaceutical Co., Ltd., Osaka, Japan

[21] Appl. No.: 206,297

[22] Filed: Jun. 14, 1988

[30] Foreign Application Priority Data

Jun. 22, 1987 [GB] United Kingdom ............... 8714596

[51] Int. Cl.$^4$ .................. A61K 31/495; C07D 417/14
[52] U.S. Cl. .................................... 514/253; 544/362
[58] Field of Search ........................... 544/362, 253

[56] References Cited

U.S. PATENT DOCUMENTS 3,661,921  5/1972  Umio ................................. 544/368

FOREIGN PATENT DOCUMENTS 0232740  8/1987  European Pat. Off. .

OTHER PUBLICATIONS

Otsuka Pharmaceutical Factory Inc., CA 101-171287g (1984), Carboxaminothiazolopyridines.
Whittle et al., Chem. Abst. 107-236728X.
Chemical Abstracts, vol. 101, 1984, pp. 706-707, Abstract No. 171287g.
Japanese Journal of Pharmacology, vol. 30, 1980, pp. 905-912, Takano et al.: Inhibitory Effect of Tiaramide on Aggregation . . .

Primary Examiner—Cecilia Shen
Attorney, Agent, or Firm—Oblon, Spivak, McClelland, Maier & Neustadt

[57] ABSTRACT

An antithrombotic compound of the formula:

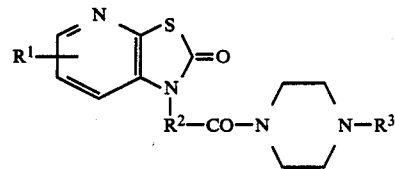

wherein
$R^1$ is halogen,
$R^2$ is lower alkylene and
$R^3$ is lower alkyl, hydroxy(lower)alkyl, acyloxy (lower)alkyl or acyl(lower)alkyl, and
pharmaceutically acceptable salts thereof.

5 Claims, No Drawings

THIAZOLOPYRIDINE COMPOUNDS, PROCESSES FOR THE PREPARATION THEREOF AND PHARMACEUTICAL COMPOSITION COMPRISING THE SAME

This invention relates to new thiazolopyridine compounds. More particularly, this invention relates to new thiazolopyridine compounds and pharmaceutically acceptable salts thereof which have pharmacological activities, processes for preparation thereof, a pharmaceutical composition comprising the same and method of use thereof.

Accordingly, one object of this invention is to provide the new and useful thiazolopyridine compounds and pharmaceutically acceptable salts thereof.

Another object of this invention is to provide processes for preparation of the thiazolopyridine compounds and pharmaceutically acceptable salts thereof.

A further object of this invention is to provide a pharmaceutical composition comprising said thiazolopyridine compounds or a pharmaceutically acceptable salt thereof.

Still further object of this invention is to provide a method of using said thiazolopyridine compounds or a pharmaceutically acceptable salt thereof for therapeutic treatment of thrombosis in human being and animals.

With regard to the state of the art in this field, 5-chloro-3-{[4-(2-hydroxyethyl)-1-piperazinyl]carbonylmethyl}-2-benzothiazolinone hydrochloride (generic name: Tiaramide hydrochloride) has been well known as anti-inflammatory drug.

The antithrombotic activity of said compound has also been known as described in the Japanese Journal of Pharmacology [Volume 30, Page 905–912, (1980)]. Further, the following thiazolopyridine compounds have been known (Japanese Unexamined Patent Publication No. 95290/1984).

(i)  2-Oxo-1-[{2-(4-methyl-1-piperazinyl)carbonyl}ethyl]1,2-dihydrothiazolo[5,4-b]pyridine (ii) 2-Oxo-1-[{4-(2-hydroxyethyl)-1-piperazinyl}carbonylmethyl]-1,2-dihydrothiazolo[5,4-b]pyridine However, the antithrombotic activity of said two compounds have not been known.

The object thiazolopyridine compounds of this invention are novel and represented by the following general formula [I]:

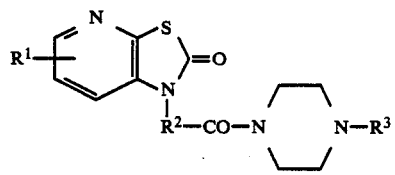

[I]

wherein
$R^1$ is halogen,
$R^2$ is lower alkylene and
$R^3$ is lower alkyl, hydroxy(lower)alkyl, acyloxy(lower)alkyl or acyl(lower)alkyl.

The object compound [I] of the present invention can be prepared by the following processes.

Process 1

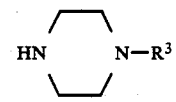

[III]
or its reactive derivative at the amino group or its salt

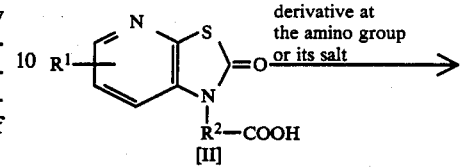

[II]
or its reactive derivative at the carboxy group or its salt

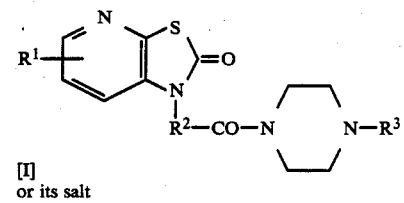

[I]
or its salt

Process 2

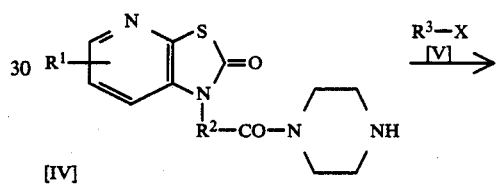

[IV]
or its salt

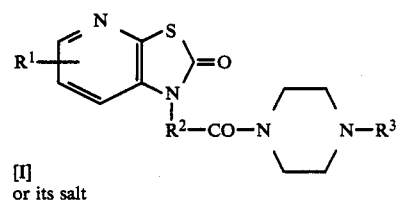

[I]
or its salt

Process 3

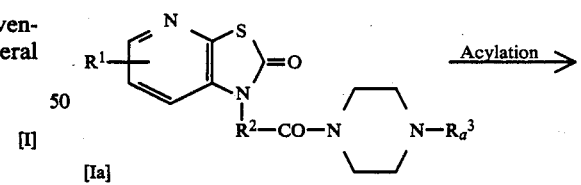

[Ia]
or its salt

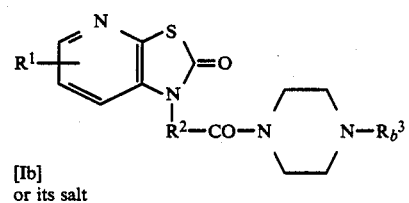

[Ib]
or its salt wherein
$R^1$, $R^2$ and $R^3$ are each as defined above,
$R_a^3$ is hydroxy(lower)alkyl,
$R_b^3$ is acyloxy(lower)alkyl, and
X is leaving group.

In the above and subsequent description of the present specification, suitable examples and illustrations for the various definitions to be included within the scope of the invention are explained in detail as follows:

The term "lower" is intended to mean 1 to 6 carbon atom(s) unless otherwise indicated.

Suitable examples of the lower alkyl may be a straight or branched one such as methyl, ethyl, propyl, isopropyl, butyl, isobutyl, tert-butyl, pentyl, hexyl or the like.

Suitable example of "lower alkyl" moiety in the terms "hydroxy(lower)alkyl", "acyl(lower)alkyl" and "acyloxy(lower)alkyl" can be referred to the ones as exemplified above.

Suitable examples of the lower alkylene group may be a straight or branched one such as methylene, ethylene, trimethylene, tetramethylene, pentamethylene, hexamethylene, propylene, methylethylene, ethylethylene, propylethylene, isopropylethylene, methylpentamethylene or the like.

Suitable examples of "halogen" may include chlorine, bromine, iodine and fluorine.

Suitable examples of acyl moiety in the terms "acyloxy(lower)alkyl" and "acyl(lower)alkyl" may include lower alkanoyl [e.g. formyl, acetyl, propionyl, valeryl, pivaloyl, etc.], lower alkoxycarbonyl [e.g. methoxycarbonyl, ethoxycarbonyl, propoxycarbonyl, isopropoxycarbonyl, butoxycarbonyl, t-butoxycarbonyl, pentyloxycarbonyl, hexyloxycarbonyl, etc.], lower alkanesulfonyl [e.g. methanesulfonyl, ethanesulfonyl, propanesulfonyl, butanesulfonyl, pentanesulfonyl, hexanesulfonyl, etc.], aroyl [e.g. benzoyl, naphthoyl, etc.] arylcarbamoyl [e.g. phenylcarbamoyl, tolylcarbamoyl, etc.] and the like.

Suitable "leaving group" may include hydroxy and acid residue, and suitable example of "acid residue" may be halogen (e.g. chlorine, bromine, iodine, or fluorine), sulfonyloxy (e.g. methanesulfonyloxy, benzenesulfonyloxy, toluenesulfonyloxy, etc.), or the like, in which the preferred example may be halogen.

Suitable pharmaceutically acceptable salts of the object compound [I] are conventional non-toxic salts and include an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, ornithine salt, etc.], a salt with base such as alkali metal salt [e.g. sodium salt, potassium salt, etc.] an alkaline earth metal salt [e.g. calcium salt, magnesium salt, etc.] or the like, and the like.

In this respect it is to be noted that the compounds [Ia] and [Ib] are included within the scope of the compound [I], and accordingly the suitable salts of these compounds [Ia] and [Ib] are to be referred to those as exemplified for the object compound [I] in the above.

The processes for preparing the object compound [I] or salts thereof are explained in detail in the following.

PROCESS 1

The object compound [I] or its salt can be prepared by reacting the compound [II] or its reactive derivative at the carboxy group or its salt with the compound [III] or its reactive derivative at the amino group or its salt.

Suitable reactive derivative at the carboxy group of the compound [II] may include an acid halide, an acid anhydride, an amide, an ester and the like.

Suitable examples of such reactive derivatives may be acid chloride, an acid azide, a mixed acid anhydride with an acid such as substituted phosphoric acid [e.g. dialkylphosphoric acid, phenylphosphoric acid, etc.], alphatic carboxylic acid [e.g. pivalic acid, acetic acid, trichloroacetic acid, etc.] or the like, a symmetrical acid anhydride, an amide with imidazole, triazole or dimethylpyrazole, an ester such as lower alkyl ester (e.g., methyl ester, ethyl ester, propyl ester, etc.) or an ester with N-hydroxysuccinimide, N-hydroxyphthalimide or 1-hydroxy-6-chlorobenzotriazole, and the like.

Suitable reactive derivatives at the amino group of the compound [III] include conventional ones used in amidation, for example, Schiff's base type imino or its tautomeric enamine type isomer formed by reaction of the compound [III] with a carbonyl compound, a silyl derivative formed by reaction of the compound [III] with a silyl compound such as trimethylsilylacetamide, bis(trimethylsilyl)acetamide or the like, a derivative formed by reaction of the compound [III] with phosphorus trichloride or phosgene, and the like.

This reaction may be carried out in the presence of a conventional condensing agent such as N,N-dicyclohexylcarbodiimide; phosphorus oxychloride; phosphorus trichloride; phosphorus pentachloride; thionyl chloride; oxalyl chloride; 1-(p-chlorobenzenesulfonyloxy)-6-chloro-1H-benzotriazole; so-called Vilsmeier, for example (chloromethylene) dimethylammonium chloride produced by the reaction of dimethylformamide with thionyl chloride or phosgene, a compound produced by the reaction of dimethylformamide with phosphorous oxychloride, etc.; or the like.

This reaction is usually carried out in a conventional solvent such as water, methanol, ethanol, propanol, tetralin, tetrahydrofuran, dioxane, chloroform, acetone, toluene, dimethylformamide, dimethylsulfoxide, methylene chloride or any other organic solvent which does not adversely influence the reaction.

The reaction temperature is not critical, and the reaction is usually carried out under cooling, at ambient temperature, under warming or under heating.

PROCESS 2

The object compound [I] or its salt can be prepared by reacting the compound [IV] or its salt with the compound [V].

The present reaction is preferably carried out in the presence of a base such as an inorganic base or an organic base for example, alkali metal hydride [e.g. sodium hydride, potassium hydride, etc.], alkaline earth metal hydride [e.g. calcium hydride, magnesium hydride, etc.], alkali metal hydroxide [e.g. sodium hydroxide, potassium hydroxide, etc.], alkali metal carbonate [e.g. sodium carbonate, potassium carbonate, etc.], alkali metal bicarbonate [e.g. sodium bicarbonate, potassium bicarbonate, etc.], alkali metal fluoride [e.g. potassium fluoride, cesium fluoride, etc.], alkali metal alkoxide [e.g. sodium methoxide, sodium ethoxide, potassium tert-butoxide, etc.], trialkylamine [e.g. trimethylamine, triethylamine, etc.], picoline, 1,5-diazabicyclo[4,3,0]-non-5-ene, 1,4-diazabicyclo[2,2,2]octane, 1,5-diazabicyclo[5,4,0]undecent-5 or the like.

This reaction is usually carried out in a conventional solvent such as water, methanol, ethanol, propanol, tetralin, tetrahydrofuran, dioxane, chloroform, toluene, N,N-dimethylformamide, dimethylsulfoxide or any other organic solvent which does not adversely influence the reaction.

The reaction temperature is not critical, and the reaction is usually carried out under cooling, at ambient temperature or under heating.

PROCESS 3

The object compound [Ib] or its salt can be prepared by acylating a compound [Ia] or its salt.

Suitable acylating agent to be used in this reaction includes an organic acid such as alkanoic acid [e.g. formic acid, acetic acid, propionic acid, etc.], arenecarboxylic acid (e.g. benzoic acid, toluenecarboxylic acid, etc.) which may have halogen, lower alkanesulfonic acid [e.g. methanesulfonic acid, etc], arylisocyanate [e.g. phenylisocyanate, etc.] which may have halogen and its reactive derivative.

The suitable reactive derivative may be a conventional one such as an acid halide [e.g. acid chloride, acid bromide, etc.], an acid azide, an acid anhydride, an activated amide, an activated ester and the like.

When free acid is used as an acylating agent, the acylation reaction may preferably be conducted in the presence of a conventional condensing agent as mentioned above for Process 1.

The reaction can preferably be conducted in the presence of an organic or inorganic base as explained in Process 2.

This reaction is usually carried out in a solvent which does not adversely influence the reaction such as water, methanol, ethanol, propanol, tetrahydrofuran, chloroform, dioxane, pyridine, methylene chloride or the like.

The reaction temperature is not critical and the reaction can be carried out under cooling to heating.

The compounds thus obtained by Processes 1 to 3 may be converted into aforesaid pharmaceutically acceptable salts thereof according to a conventional manner.

The new thiazolopyridine compounds [I] and pharmaceutical acceptable salts thereof possess antithrombotic activity, and are useful for a therapeutic treatment of thrombosis [e.g. cerebral thrombosis, etc.].

For the purpose of showing pharmaceutical activity of the thiazolopyridine compounds [I], pharmacological test data of the representative compounds of the thiazolopyridine compounds [I] are illustrated in the following.

PLATELET AGGREGATION IN VITRO

1. Test method

Platelet rich plasma (PRP) which contains $6-7 \times 10^8$ platelets/ml was prepared from rabbit blood. To the 200 $\mu$l of PRP, 5 $\mu$l of calcium chloride (1 mM) and 50 $\mu$l of 25 mM Tris-acetate solution (pH 7.4) containing 120 mM NaCl or test compound were added successively, and then stirred for 2 min. at 37° C. To the solution, 5 $\mu$l of adenosine diphosphate (ADP) (2.5 $\mu$M) or collagen (2.5 $\mu$g/ml) was added to an aggregation inducer. Aggregation was measured by using an aggregometer (NKK HEMATRACER 1). Activities of inhibitors (test compounds) were expressed as ID$_{50}$ values i.e. Doses required to inhibit the platelet aggregation responses by 50%.

2. Test result

| Test compound | ID$_{50}$ (M) | |
|---|---|---|
| | ADP | Collagen |
| Example 2 | $5.5 \times 10^{-5}$ | $3.7 \times 10^{-5}$ |

PLATELET AGGREGATION EX VIVO

1. Test method

Male Sprague-Dawley rats weighing about 250 g were used after overnight fasting. One hour after oral administration of test compound or vehicle of test compound (control), blood was collected into a tube containing 0.1 vol. of 3.8% sodium citrate. To the 0.45 ml of blood, 0.05 ml of collagen (final concentration 5.0 $\mu$g/ml) was added and then incubated for 5 min. at 37° C. under shaking.

The reaction was terminated by addition of 1 ml of 10 mM phosphate buffered saline (pH 7.4) containing 11.5 mM EDTA and 1% formalin. The reaction mixture was centrifuged at 70 xg for 5 min. and platelet count of upper phase was measured by Technicon Auto Analizer.

Platelet aggregation was calculated according to the following formula:

$$\text{Platelet aggregation (\%)} = \frac{A - B}{A} \times 100$$

A; Platelet count after addition of vehicle of collagen
B; Platelet count after addition of collagen
Inhibition of the test compound was calculated according to the following formula;

$$\text{Inhibition (\%)} = \frac{C - D}{C} \times 100$$

C; Platelet aggregation (%) of control
D; Platelet aggregation (%) of Test compound 2. Test result

| Test compound | Dose (mg/kg) | Inhibition (%) |
|---|---|---|
| Example 2 | 10 | 8 |
| | 32 | 103 |
| | 100 | 121 |

For therapeutic administration, the object compounds [I] of the present invention and pharmaceutically acceptable salts thereof are used in a form of the conventional pharmaceutical preparation is admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion. If needed, there may be included in the above preparation auxiliary substance such as stabilizing agent, wetting or emulsifying agent, buffer or any other commonly used additives.

The effective ingredient may usually be administered with a unit dose of 0.01 mg/kg to 500 mg/kg, 1 to 4 times a day. However, the above dosage may be increased or decreased according to age, weight and conditions of the patient or the administering method.

The following preparations and examples are given only for the purpose of illustrating the present invention in more detail.

PREPARATION 1

3-Amino-5-chloro-2-mercarptopyridine (18.8 g) was added to an ice-cooled solution of phosgene (30 g) in toluene (350 ml). 10% aqueous solution of sodium hydroxide (300 ml) was added dropwise to the stirred mixture for a period of 1 hour below 20° C. The final mixture was stirred for 1.5 hours at ambient temperature and then stirred for an additional 1 hour at 50° C. After cooling, the aqueous layer was adjusted to pH 4.0 with 4N hydrochloric acid. The precipitates were collected by filtration, washed with water and dried over phosphorus pentoxide to give white power of 6-chloro-2-oxo-1,2-dihydrothiazolo[5,4-b]pyridine (15.08 g).

IR (Nujol): 3150, 3100, 3000, 1660, 1590, 1210, 1120, 900 cm$^{-1}$.

NMR (DMSO-d$_6$, δ): 7.50 (1H, d, J=2 Hz), 8.27 (1H, d, J=2 Hz).

PREPARATION 2

In a similar manner to that of Preparation 1, there was obtained the following compound.
5-chloro-2-oxo-1,2-dihydrothiazolo[5,4-b]pyridine
mp: >250° C.
IR (Nujol): 3150, 1670, 1400, 1215, 1110 cm$^{-1}$.
NMR (DMSO-d$_6$, δ): 7.46 (1H, d, J=2.0 Hz), 8.22 (1H, d, J=2.0 Hz).

PREPARATION 3

Methyl chloroacetate (9.6 g) and potassium carbonate (11.1 g) were added to a solution of 6-chloro-2-oxo-1,2-dihydrothiazolo[5,4-b]pyridine (15.0 g) in dry N,N-dimethylformamide (50 ml). The mixture was stirred for 30 minutes at 80° C. and then poured into cold water. The precipitates were collected by filtration, washed with water and dried over phosphorus pentoxide to give white power of 6-chloro-1-methoxycarbonylmethyl-2-oxo-1,2-dihydrothiazolo[5,4-b]pyridine (20.52 g).

IR (Nujol): 1740, 1690, 1590, 1310, 1230, 1180, 960, 900, 880, 710 cm$^{-1}$.

NMR (CDCl$_3$, δ): 3.70 (3H, s), 4.65 (2H, s), 7.15 (1H, d, J=2 Hz), 8.23 (1H, d, J=2 Hz).

PREPARATION 4

In a similar manner to that of Preparation 3, there was obtained the following compound.
5-Chloro-1-methoxycarbonylmethyl-2-oxo-1,2-dihydrothiazolo[5,4-b]pyridine
mp: 138°-140° C.
IR (Nujol): 1740, 1690, 1585, 1230, 1185, 720 cm$^{-1}$.
NMR (DMSO-d$_6$, δ): 3.70 (3H, s), 4.87 (2H, s), 8.10 (1H, d, J=2.0 Hz), 8.40 (1H, d, J=2.0 Hz).

EXAMPLE 1

A mixture of 6-chloro-1-methoxycarbonylmethyl-2-oxo-1,2-dihydrothiazolo[5,4-b]pyridine (10.32 g) and N-(2-hydroxyethyl)piperazine (10.4 g) was heated at 130° C. for 15 min. After cooling, the reaction mixture was poured into an ice-water. The precipitates obtained were extracted with chloroform. The chloroform layer was dried over magnesium sulfate, and evaporated to give crude material. The crude material was purified on a silica gel column chromatography using a mixture of methylene chloride and methanol (10:1). The desired fractions containing the objective compound were collected and evaporated. The crude crystals obtained were recrystallized from a mixture of methanol and diethyl ether to give 6-chloro-2-oxo-1-{[4-(2-hydroxyethyl)-1-piperazinyl]carbonylmethyl}-1,2-dihydrothiazolo[5,4-b]pyridine (5.70 g).

mp: 198°-200° C.

IR (Nujol): 3500, 1695, 1660, 1580, 1400, 1050, 790 cm$^{-1}$.

NMR (DMSO-d$_6$, δ): 2.35 (4H, m), 3.3-3.6 (8H, m), 4.36 (1H, t, J=5 Hz), 4.94 (2H, s), 7.92 (1H, d, J=2 Hz), 8.33 (1H, d, J =2 Hz).

EXAMPLE 2

A mixture of 6-chloro-1-methoxycarbonylmethyl-2-oxo-1,2-dihydrothiazolo[5,4-b]pyridine (2.0 g) and N-methyl-piperazine (1.6 g) was heated at 130° C. for 15 min. After cooling, the mixture was purified on a silica gel column chromatography using a mixture of chloroform and methanol (10:1). The desired fractions containing the objective compound were collected and evaporated. The crude crystals obtained were recrystallized from a mixture of chloroform and diethyl ether to give 6-chloro-2-oxo-1-[(4-methyl-1-piperazinyl)carbonylmethyl]-1,2-dihydrothiazolo[5,4-b]pyridine (0.4 g).

mp: 198°-200° C.

IR (Nujol): 1670, 1645, 1580, 1450, 1295, 1230, 875, 805 cm$^{-1}$.

NMR (DMSO-d$_6$, δ): 2.23 (3H, s), 2.30 (4H, m), 3,55 (4H, m), 4.96 (2H, s), 7.96 (1H, d, J=2 Hz), 8.36 (1H, d, J=2 Hz).

EXAMPLE 3

A mixture of 6-chloro-1-carboxymethyl-2-oxo-1,2-dihydrothiazolo[5,4-b]pyridine (8.1 g) and thionyl chloride (50 ml) was heated under refluxing for 1 hour. After removed of the excess of thionyl chloride, the corresponding acid chloride obtained was used for the next reaction without further purification. To a stirred solution of N-methylpiperazine (3.4 g) in a mixture of acetone (50 ml) and water (15 ml), a solution of the acid chloride in acetone (35 ml) was added dropwise over 10 min. at the room temperature. The resultant mixture was stirred for 2.5 hours, concentrated, and then diluted with 5% sodium hydroxide. The precipitates obtained were filtered and washed twice with water. The crude crystals were recrystallized from methanol to give 6-chloro-2-oxo-1-[(4-methyl-1-piperazinyl)carbonylmethyl]-1,2-dihydrothiazolo[5,4-b]pyridine (7.0 g).

mp: 201°-203° C.

Elemental analysis Calcd. for C$_{13}$H$_{15}$ClN$_4$O$_2$S: C, 47.78; H, 4.63; N, 17.14, Found: C, 47.91; H, 4.47; N, 17.23.

EXAMPLE 4

In a similar manner to that of Example 1, 2 or 3, there were obtained the following compounds.
(1) 5-Chloro-2-oxo-1-{[4-(2-hydroxyethyl)-1-piperazinyl]carbonylmethyl}-1,2-dihydrothiazolo[5,4-b]pyridine
mp: 164°-166° C.
IR (Nujol): 3160, 1705, 1650, 1210, 825 cm$^{-1}$.
NMR (DMSO-d$_6$, δ): 2.40-2.60 (6H, m), 3.46 (6H, m), 4.36 (1H, t, J=5 Hz), 4.96 (2H, s), 7.46 (1H, d, J=8 Hz), 7.73 (1H, d, J=8 Hz).
(2) 5-Chloro-2-oxo-[(4-methyl-1-piperazinyl)carbonylmethyl]-1,2-dihydrothiazolo[5,4-b]pyridine
mp: 188°-190° C.

IR (Nujol): 1680, 1660, 1585, 1210, 825 cm⁻¹.

NMR (DMSO-d₆, δ): 2.30 (3H, s), 2.45 (4H, m), 3.5— (4H, m), 4.69 (2H, s), 7.23 (2H, s).

(3) 6-Chloro-2-oxo-1-[(4-acetonyl-1-piperazinyl)carbonylmethyl]-1,2-dihydrothiazolo[5,4-b]pyridine
mp: 191°–193° C.

IR (Nujol): 1720, 1700, 1645, 1585, 1420, 1295, 905, 790 cm⁻¹.

NMR (CDCl₃, δ): 2.20 (3H, s), 2.50 (4H, m), 3.26 (2H, s), 3.66 (4H, m), 4.69 (2H, s), 7.26 (1H, d, J=2 Hz), 8.23 (1H, d, J=2 Hz).

(4) 6-Chloro-2-oxo-1-{[4-(2-acetoxyethyl)-1-piperazinyl]carbonylmethyl}-1,2-dihydrothiazolo[5,4-b]pyridine
mp: 153°–155° C.

IR (Nujol): 1705, 1658, 1580, 1465, 1250, 1185, 1030, 1000 cm⁻¹.

NMR (DMSO-d₆, δ): 2.00 (3H, s), 2.50 (6H, m), 3.50 (4H, m), 4.16 (2H, t), 4.96 (2H, s), 7.92 (1H, t, J=2.0 Hz), 8.33 (1H, d, J=2.0 Hz).

(5) 5-Chloro-2-oxo-1-{[4-(2-acetoxyethyl)-1-piperazinyl]carbonylmethyl}-1,2-dihydrothiazolo[5,4-b]pyridine
mp: 101°–102.5° C.

IR (Nujol): 1740, 1210, 1705, 1650 cm⁻¹.

NMR (CDCl₃, δ): 7.25 (2H, s), 4.72 (2H, s), 4.20 (2H, t, J=6 Hz), 3.60 (4H, t, J=5 Hz), 2.65 (2H, t), 2.50 (4H, t), 2.07 (3H, s).

EXAMPLE 5

A mixture of 6-chloro-2-oxo-1-(1-piperazinyl)carbonylmethyl-1,2-dihydrothiazolo[5,4-b]pyridine (0.80 g), chloroacetone (0.24 g), and potassium carbonate (0.35 g) in dry N,N-dimethylformamide (2.4 ml) was heated at 80° C. for 30 min. The mixture was poured into an ice-water, and the precipitates obtained were extracted with chloroform. The chloroform layer was washed with water, dried over magnesium sulfate, and evaporated to give crude crystals (0.85 g). The crude crystals were recrystallized from a mixture of chloroform and ethyl acetate to give 6-chloro-2-oxo-1-[(4-acetonyl-1-piperazinyl)carbonylmethyl]-1,2-dihydrothiazolo[5,4-b]pyridine (0.45 g).

mp: 191°–193° C.

IR (Nujol): 1720, 1700, 1645, 1585, 1420, 1295, 905, 790 cm⁻¹.

NMR (CDCl₃, δ): 2.20 (3H, s), 2.50 (4H, m), 3.26 (2H, s), 3.66 (4H, m), 4.69 (2H, s), 7.26 (1H, d, J=2 Hz), 8.23 (1H, d, J=2 Hz).

EXAMPLE 6

In a similar manner to that of Example 5, there were obtained the following compounds.

(1) 6-Chloro-2-oxo-1-{[4-(2-hydroxyethyl)-1-piperazinyl]carbonylmethyl}-1,2-dihydrothiazolo[5,4-b]pyridine
mp: 198°–200° C.

IR (Nujol): 3500, 1695, 1660, 1580, 1400, 1050, 790 cm⁻¹.

NMR (DMSO-d₆, δ): 2.35 (4H, m), 3.3–3.6 (8H, m), 4.36 (1H, t, J=5 Hz), 4.94 (2H, s), 7.92 (1H, d, J=2 Hz), 8.33 (1H, d, J=2 Hz).

(2) 5-Chloro-2-oxo-1-{[4-(2-hydroxyethyl)-1-piperazinyl]carbonylmethyl}-1,2-dihydrothiazolo[5,4-b]pyridine
mp: 164°–166° C.

IR (Nujol): 3160, 1705, 1650, 1210, 825 cm⁻¹.

NMR (DMSO-d₆, δ): 2.40–2.60 (6H, m), 3.46 (6H, m), 4.36 (1H, t, J=5 Hz), 4.96 (2H, s), 7.46 (1H, d, J=8 Hz), 7.73 (1H, d, J=8 Hz).

(3) 6-Chloro-2-oxo-1-[(4-methyl-1-piperazinyl)carbonylmethyl]-1,2-dihydrothiazolo[5,4-b]pyridine
mp: 198°–200° C.

IR (Nujol): 1670, 1645, 1580, 1450, 1295, 1230, 875, 805 cm⁻¹.

NMR (DMSO-d₆, δ): 2.23 (3H, s), 2.30 (4H, m), 3,55 (4H, m), 4.96 (2H, s), 7.96 (1H, d, J=2 Hz), 8.36 (1H, d, J=2 Hz).

(4) 5-Chloro-2-oxo-1-[(4-methyl-1-piperazinyl)carbonylmethyl]-1,2-dihydrothiazolo[5,4-b]pyridine
mp: 188°–190° C.

IR (Nujol): 1680, 1660, 1585, 1210, 825 cm⁻¹.

NMR (DMSO-d₆, δ): 2.30 (3H, s), 2.45 (4H, m), 3.56 (4H, m), 4.69 (2H, s), 7.23 (2H, s).

(5) 6-Chloro-2-oxo-1-{[4-(2-acetoxyethyl)-1-piperazinyl]carbonylmethyl}-1,2-dihydrothiazolo[5,4-b]pyridine
mp: 153°–155° C.

IR (Nujol): 1705, 1658, 1580, 1465, 1250, 1185, 1030, 1000 cm⁻¹.

NMR (DMSO-d₆, δ): 2.00 (3H, s), 2.50 (6H, m), 3.50 (4H, m), 4.16 (2H, t), 4.96 (2H, s), 7.92 (1H, d, J=2.0 Hz), 8.33 (1H, d, J=20 Hz).

(6) 5-Chloro-2-oxo-1-{[4-(2-acetoxyethyl)-1-piperazinyl]carbonylmethyl}-1,2-dihydrothiazolo[5,4-b]pyridine
mp: 101°–102.5° C.

IR (Nujol): 1740, 1210, 1705, 1650 cm⁻¹.

NMR (CDCl₃, δ): 7.25 (2H, s), 4.72 (2H, s), 4.20 (2H, t, J=6 Hz), 3.60 (4H, t, J=5 Hz), 2.65 (2H, t), 2.50 (4H, t), 2.07 (3H, s).

EXAMPLE 7

To an ice-cooled solution of 6-chloro-2-oxo-1-{[4-(2-hydroxyethyl)-1-piperazinyl]carbonylmethyl]-1,2-dihydrothiazolo[5,4-b]pyridine (1.35 g) in dry pyridine (10 ml), acetic anhydride (0.73 g) was added dropwise and then the mixture was stirred at the temperature for 2 hours and at the room temperature for 4 hours. After removal of the solvent, the residual oil obtained was purified on an aluminum-oxide column chromatography using a mixture of chloroform and n-hexane (2:1). The fractions containing the objective compound were collected and evaporated to give crude crystals. The crude crystals were recrystallized from ethyl acetate to afford 6-chloro-2-oxo-1-{[4-(2-acetoxyethyl)-1-piperazinyl]carbonylmethyl}-1,2-dihydrothiazolo[5,4-b]pyridine (1,2 g).

mp: 153°–155° C.

IR (Nujol): 1705, 1658, 1580, 1465, 1250, 1185, 1030, 1000 cm⁻¹.

NMR (DMSO-d₆, δ): 2.00 (3H, s), 2.50 (6H, m), 3.50 (4H, m), 4.16 (2H, t), 4.96 (2H, s), 7.92 (1H, d, J=2.0 Hz), 8.33 (1H, d, J=2.0 Hz).

EXAMPLE 8

In a similar manner to that of Example 7, there was obtained the following compound.

5-Chloro-2-oxo-1-{[4-(2-acetoxyethyl)-1-piperazinyl]carbonylmethyl}-1,2-dihydrothiazolo[5,4-b]pyridine
mp: 101°–102.5° C.

IR (Nujol): 1740, 1210, 1705, 1650 cm⁻¹.

NMR (CDCl₃, δ): 7.25 (2H, s), 4.72 (2H, s), 4.20 (2H, t, J=6 Hz), 3.60 (4H, t, J=5 Hz), 2.65 (2H, t), 2.50 (4H, t), 2.07 (3H, s).

What we claim is:

1. A compound of the formula:

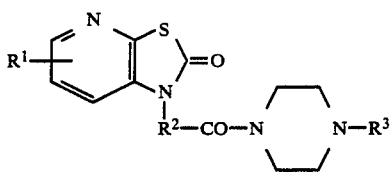

wherein
R¹ is halogen,
R² is lower alkylene and
R³ is lower alkyl, hydroxy(lower)alkyl, acyloxy(lower)alkyl or acyl(lower)alkyl, and
pharmaceutically acceptable salts thereof.

2. A compound of claim 1, wherein R³ is lower alkyl.

3. A compound of claim 2, which is 6-chloro-2-oxo-1-[(4-methyl-1-piperazinyl)carbonylmethyl]-1,2-dihydrothiazolo[5,4-b]pyridine.

4. An antithrombotic pharmaceutical composition comprising, as an active ingredient, an effective amount of a compound of claim 1 or pharmaceutically acceptable salt thereof in association with a pharmaceutically acceptable carrier or excipient.

5. A method for the treatment of thrombosis in a human being or animal comprising administering an antithrombotically effective amount of a compound of claim 1 or pharmaceutically acceptable salt thereof.

* * * * *